United States Patent
Ries

(10) Patent No.: US 9,649,500 B2
(45) Date of Patent: May 16, 2017

(54) SHIELD FORMING TO FACILITATE TIGHT RADIUS AT WELD SEAM USING PROGRESSIVE STAMPING

(71) Applicant: Medtronic, Inc., Minneapolis, MN (US)

(72) Inventor: Andrew J. Ries, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 334 days.

(21) Appl. No.: 14/257,088

(22) Filed: Apr. 21, 2014

(65) Prior Publication Data

US 2015/0297897 A1  Oct. 22, 2015

(51) Int. Cl.
| | | |
|---|---|---|
| *A61B 19/02* | (2006.01) | |
| *A61N 1/375* | (2006.01) | |
| *A61B 5/00* | (2006.01) | |
| *A61B 46/13* | (2016.01) | |
| *A61B 50/30* | (2016.01) | |
| *A61B 46/10* | (2016.01) | |
| *A61B 17/00* | (2006.01) | |
| *A61M 5/142* | (2006.01) | |

(52) U.S. Cl.
CPC ............. *A61N 1/375* (2013.01); *A61B 5/686* (2013.01); *A61B 46/10* (2016.02); *A61B 46/13* (2016.02); *A61B 50/30* (2016.02); *A61B 2017/00526* (2013.01); *A61B 2560/0406* (2013.01); *A61B 2562/12* (2013.01); *A61M 5/14276* (2013.01); *A61M 2207/00* (2013.01)

(58) Field of Classification Search
CPC ........ A61N 1/375; A61B 46/10; A61B 46/13; A61B 50/30; A61B 5/686; A61B 5/00; A61B 2560/0406; A61B 2562/12; A61M 5/1413

See application file for complete search history.

(56) References Cited

U.S. PATENT DOCUMENTS

| | | | | |
|---|---|---|---|---|
| 4,759,463 A | * | 7/1988 | Mazoin | B65D 43/0272 220/270 |
| 5,456,698 A | * | 10/1995 | Byland | A61N 1/375 607/36 |
| 6,249,423 B1 | * | 6/2001 | O'Phelan | H01G 9/008 29/25.03 |
| 7,012,799 B2 | * | 3/2006 | Muffoletto | H01G 9/06 29/25.03 |
| 7,801,613 B2 | | 9/2010 | Li et al. | |
| 7,912,549 B2 | | 3/2011 | Mueller et al. | |
| 8,065,007 B2 | * | 11/2011 | Ries | A61N 1/3968 607/36 |
| 9,283,302 B2 | * | 3/2016 | Matheny | A61L 31/16 |
| 2004/0062985 A1 | * | 4/2004 | Aamodt | H01M 2/0207 429/176 |
| 2004/0147974 A1 | | 7/2004 | Engmark et al. | |
| 2006/0259091 A1 | * | 11/2006 | Ries | A61N 1/3968 607/36 |

(Continued)

Primary Examiner — Hanh V Tran

(57) ABSTRACT

A method for manufacturing a medical device housing includes deforming an inner surface of a shield member to produce a seam area along the inner surface. The shield member has an inner surface and an outer surface spaced apart by a shield thickness. A seam seals the inner surface seam area of the shield member to a second shield member. The shield member inner surface has a bend extending to an interior edge of the seam.

12 Claims, 6 Drawing Sheets

(56) References Cited

U.S. PATENT DOCUMENTS

| | | |
|---|---|---|
| 2008/0186691 A1 | 8/2008 | Mertz et al. |
| 2010/0274309 A1* | 10/2010 | Knipfer .................. A61N 1/375 607/36 |
| 2013/0116763 A1* | 5/2013 | Parker ................ A61N 1/36071 607/117 |
| 2014/0256184 A1* | 9/2014 | Sweeney ................ A61N 1/375 439/625 |
| 2016/0121125 A1* | 5/2016 | Kast ..................... A61N 1/3754 607/116 |

* cited by examiner

SHIELD FORMING TO FACILITATE TIGHT RADIUS AT WELD SEAM USING PROGRESSIVE STAMPING

TECHNICAL FIELD

The disclosure relates generally to implantable medical devices and, in particular, to an implantable medical device housing and associated method of manufacture.

BACKGROUND

Numerous types of implantable medical devices (IMDs) are available for monitoring a patient and/or delivering automatic therapies, such as ECG monitors, cardiac monitors, pacemakers, defibrillators, drug delivery pumps, neurostimulators and the like. A general design goal in the manufacture of IMDs is to minimize the overall size of the IMD to promote patient comfort. Related to this goal is a desire to provide smooth exterior surfaces without sharp corners or edges that would cause patient discomfort. Additionally, it is desirable to minimize the cost and complexity of manufacturing steps used in producing IMDs.

The outer housing of the IMD encloses electronics that perform the various IMD functions such as acquiring and analyzing physiological signals, automatically delivering therapies, and wirelessly communicating with an external programmer or other device. As technological advances are made that may require additional circuitry or battery volume, efficient use of the volume enclosed by the IMD housing is important as the overall size of the IMD is reduced. The housing must also reliably shield internal electronics that could be damaged or malfunction if exposed to body fluids. A need remains for IMD housings and manufacturing methods that enable low cost manufacturing methods to be used without compromising the integrity of the housing as a shield against body fluids while still promoting patient comfort and facilitating overall IMD size reduction.

DETAILED DESCRIPTION

A housing and associated method of manufacture as disclosed herein may be implemented in a variety of implantable medical devices. The housing is a metallic material such as titanium, titanium alloy, stainless steel, stainless steel alloy, or other metal or metal alloy which is suitable for undergoing the fabrication methods described herein, among which may include, but are not limited to, stamping, cutting, and welding. The illustrative examples described herein and shown in the accompanying drawings depict two shield members that are joined to form an IMD housing defining an internal cavity for enclosing IMD components, such as one or more batteries, electronic circuits, processors, therapy delivery devices and/or physiological sensors. The housings and methods of manufacture as disclosed herein are not limited to a particular type or size of IMD.

Figure 1:
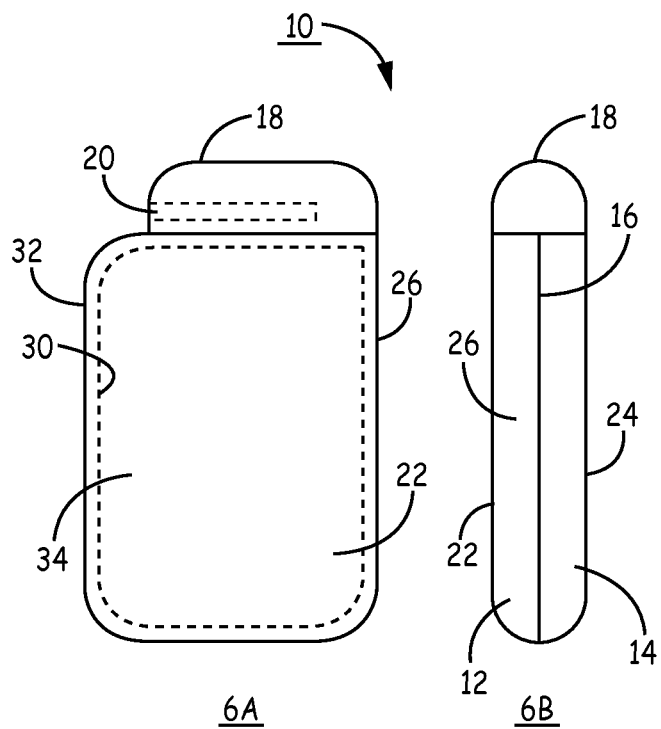
FIG. 1 is a front view and side view of one example of an IMD housing in which aspects disclosed herein may be implemented.

FIG. 1 is a front view 6A and side view 6B of one example of an IMD housing 10. Housing 10 includes a two shield members 12 and 14 joined at a seam 16. Housing 10 optionally includes a connector block 18. In some examples, IMD 10 is electrically coupled to a medical lead carrying one or more electrodes or other sensors, such as a cardiac pacing lead. To facilitate medical lead connection to internal IMD components, connector block 18 is provided with one or more connector bores 20 for receiving respective medical lead connectors which become electrically coupled to electrical feedthroughs extending across housing 10 to internal IMD circuitry. In other examples, IMD 10 is provided as a leadless device without requiring a connector block. Any required sensors and/or electrodes are incorporated within or along housing 10.

In the example shown, housing 10 has two major sides 22, 24 spaced apart by a minor sidewall 26 that defines a periphery of the housing 10. Seam 16 extends along the minor sidewall 26 in this example, joining shield members 12 and 14. Seam 16 is typically a welded seam that seals shield members 12 and 14 together after electronics have been assembled within housing 10. In other examples, seam 16 may be sealed by brazing, soldering, crimp locked with a gasket, fusion bonding or adhesive bonding. In some examples, housing 10 is a hermetically sealed housing.

Shield members 12 and 14 are formed from a sheet or block of raw material. Shield members 12 and 14 are formed into a desired contour having the depth, height and length specified to achieve a required housing volume. Shield members 12 and 14 define at least a portion of the interior housing surface 30 and exterior housing surface 32. The interior housing surface 30 defines a cavity 34 for enclosing IMD components. A low-cost manufacturing method is disclosed herein that includes progressive stamping for forming shield members 12 and 14, a deformation process to form a seam area, followed by trimming and sealing procedures that produce IMD housing 10 with a substantially smooth exterior surface along seam 16 and adequate contact between shield members 12 and 14 for a robust welding or sealing process that produces a reliable seam.

Figure 2:
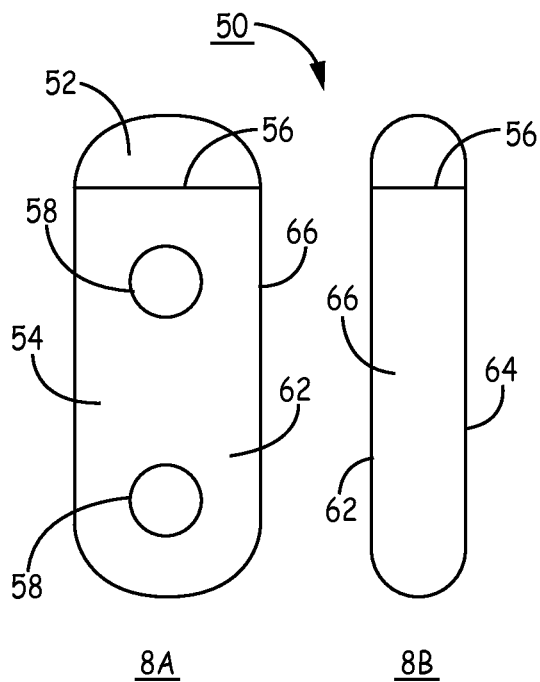
FIG. 2 is a front view and side view of another example of an IMD housing which may be manufactured using the methods disclosed herein.

FIG. 2 is a front view 8A and side view 8B of another example of an IMD housing 50. Housing 50 is a leadless device in this example, which may have one or more sensors 58 incorporated along housing 50. In this example, two shield members 52 and 54 are joined at seam 56. Seam 56 extends along major sides 62 and 64 and minor sidewall 66 extending between the major sides 62 and 64. Seam 56 is perpendicular to a major axis of the prismatic housing 50 in FIG. 2 in contrast to the seam 16 that extends parallel to a major axis of the prismatic housing 10.

The overall dimensions and shape of a housing incorporating features as disclosed herein may vary between embodiments. The seam between shield members may extend along a peripheral minor sidewall as illustrated by seam 16 in FIG. 1 and may wholly or partially circumscribe the housing. Alternatively, the seam between shield members may extend along major sides and transect the minor sidewall as illustrated by seam 56 in FIG. 2.

Further, it is recognized that two shield members sealed together to form the IMD housing may or may not be symmetrical. As illustrated in FIG. 2, the shield members 52 and 54 are not symmetrical. In FIG. 1 the shield members 12 and 14 are symmetrical. The dimensions and overall contours of the shield members may vary between embodiments, however two or more shield members will have a mating seam area formed by a deformation process as described below, along which the seam is formed to seal the shield members together to form the IMD housing. The housings 10 and 50 are shown as prismatic housings, however, it is contemplated that the manufacturing methods and associated housing aspects disclosed herein may apply to non-prismatic housings as well, such as a generally cylindrical housing.

Figure 3A:
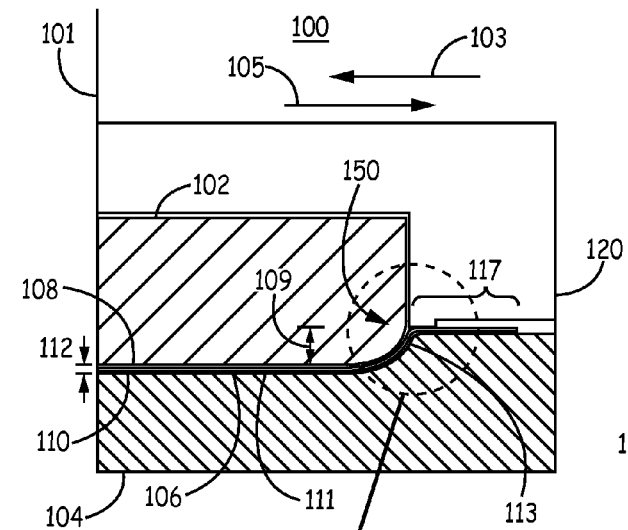
FIG. 3A is a schematic diagram of an apparatus for fabricating an IMD housing, such as the housings shown in FIG. 1 or FIG. 2.

FIG. 3A is a schematic diagram 100 of a manufacturing apparatus for fabricating an IMD housing, such as housing 10 (FIG. 1) or housing 50 (FIG. 2). Diagram 100 is a cut-away view of a housing shield member 106 and dies 102, 104. The shield member 106, and dies 102 and 104 may be symmetric with respect to line 101 such that the cut-away view represents one-half of shield 106.

A sheet of shield material is progressively stamped to form shield member 106 in one embodiment. Shield member 106 has an inner surface 108 and outer surface 110 separated by a shield thickness 112. In some examples, the shield thickness may be in the range of approximately 0.006 to approximately 0.020 inches, however practice of the techniques disclosed herein may use other shield thicknesses. Inner surface 108 will define a seam area and at least a portion of the housing interior surface and the interior cavity for housing IMD components. Outer surface 110 will define at least a portion of the housing exterior surface. As used herein, the terms "interior" and "interiorly" refer to an inward direction toward the interior cavity of the housing and symmetry line 101, as indicated by arrow 103. The terms "exterior" or "exteriorly" refer to an outward direction away from the housing interior cavity and symmetry line 101, as indicated by arrow 105.

Shield member 106 is stamped to have a major side 111 that is substantially flat in the example shown. A contoured minor sidewall 113 extends from major side 111. An outward bend 150 extends from minor sidewall 113. The remaining flat portion 117 of the shield material extending outward from bend 150 includes excess material that is trimmed away, as will described below. The shield member 106 is shown after completing a progressive stamping process in which the shield member material is stamped in multiple steps, e.g. using multiple dies, to deform a flat sheet of raw material into the shape shown, having a contoured minor sidewall 113, depth 109 and outward bend 150.

After achieving the desired contour of shield member 106, member 106 is positioned between negative support die 104 and positive clamping die 102. Dies 102 and 104 may be the final set of dies used to stamp the final contour into shield member 106. In the artist's rendering, any gaps between dies 102 and 104 and shield member 106 in FIG. 3A and in other figures presented herein are shown for clarity and would be limited within specification tolerances in practice. Dies 102 and 104 are fixed to support shield member 106 when a movable press 120 is advanced downward onto the inner surface 108 along a top surface of bend 150 and excess flat portion 117 to deform the shield member material interiorly as described in greater detail below.

Figure 3B:
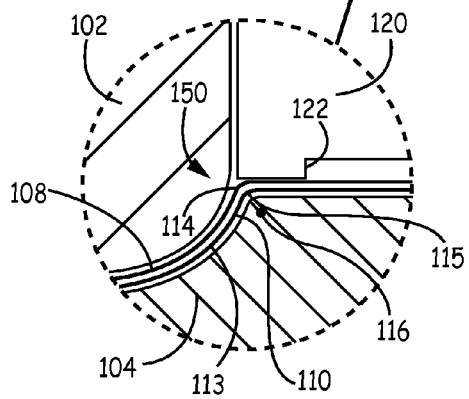
FIG. 3B is an enlarged view of a portion of the diagram of FIG. 3A.

FIG. 3B is an enlarged view of the portion shown in dashed circle in FIG. 3A. The outward bend 150 extending from sidewall 113 is defined by a bend inner surface 114 and bend outer surface 115, also seen in FIG. 4. Bend inner surface 114 has a radius 116, also referred to the inner radius 116 of bend 150. The inner radius 116 is larger than the outer radius (unnumbered in FIG. 3B for the sake of clarity but shorter than inner radius 116) of bend 150 due to the shield member thickness 112.

Figure 4:
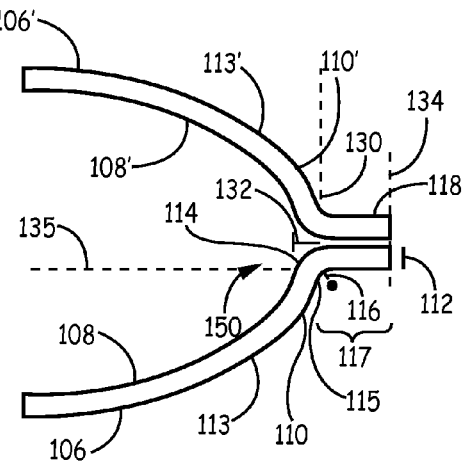
FIG. 4 is an enlarged view of a first housing shield member and a second housing shield member.

FIG. 4 is an enlarged view of a first shield member 106 and a second shield member 106', which may be identically formed within specification tolerances by progressive stamping as described in conjunction with FIG. 3A. Shield member 106' is shown inverted and aligned with shield member 106. The respective inner surfaces 108 and 108' are shown in alignment along the periphery of the shield members 106 and 106'. The shield members 106 and 106' are depicted in this manner to illustrate that the inner surfaces 108 and 108' come into direct contact exteriorly to bend inner surface 114 due to the relatively large inner radius 116 and resulting arc length of bend inner surface 114. Inner radius 116 may be approximately two times the shield member thickness 112. Typically inner radius 116 will be at least approximately equal to the shield member thickness 112 and more typically at least approximately 1.5 times the shield member thickness 112 because during the stamping process used to deform the shield material a smaller bending radius may cause tearing or fracturing of the material. If excess flat portion 117 is trimmed flush with the outer profile of sidewalls 113, 113' as defined by outer surfaces 110, 110', tangentially to the minor sidewalls 113, 113' as shown by dashed line 130, the remaining mating interface between inner surfaces 108, 108' is insufficient to form a reliable seal between shield members 106 and 106'.

For example, if excess flat portion 117 is trimmed flush with the widest point of outer surfaces 110, 110' at dashed line 130, little or no directly mating interface will remain along the inner surfaces 108, 108' due to the arc length of bend inner surface 114. Inner surfaces 108, 108' may not even make direct contact within the sidewall outer profile defined by outer surfaces 110, 110' if the excess shield material is cut away at dashed line 130, leaving no weldable seam area. The distance 132 from the interior edge of bend inner surface 114 to the direct meeting point of inner surfaces 108 and 108' approaches or exceeds the exterior location of the bend outer surface 115. Without further modification of the shield members 106 and 106', a sufficient seam area between inner surfaces 108 and 108' for forming a reliable seam would require a vertical cut to be exteriorly offset from bend outer surface 115, e.g. at dashed line 134.

Trimming excess flat portion 117 at a point that is exteriorly offset from outer surface bend 115, however, would result in an undesirable protrusion 118 along the periphery of the housing in the vicinity of the seam. To eliminate protrusion 118, which would likely cause patient discomfort, it is desirable to trim excess flat portion 117 as near to outer surfaces 110 and 110' defining the outer profile of sidewalls 113, 113' as possible, e.g. at or near a location indicated by dashed line 130.

In other examples, shield member 106 may be trimmed through minor sidewall 113, e.g. at horizontal line 135, to create a seam area along a flat end face of sidewall 113. Performing a horizontal cut through shield portion 106, however, would require removing shield member 106 from the supporting and clamping dies 102, 104 at a stamping station and positioning shield member 106 in a different fabrication station to enable trimming through the shield member 106, e.g. in a shimmy trim operation. In order to simplify the manufacturing process and eliminate or minimize manual steps of moving the shield portion 106 between fabrication stations, it is desirable to trim away excess portion 117 by performing a cut in a vertical direction, such as indicated by dashed lines 130 or 134. The excess portion 117 is accessible from above for a direct-down trimming operation when movable press 120 is raised and shield member 106 remains secured in supporting and clamping dies 102, 104. As such, it is desirable to trim excess portion 117 using a vertical cut at or near location 130, but a sufficient seam area must be established between inner surfaces 108, 108' interiorly to the cut location 130 to produce a weldable seam area that reliably joins shield members 106 and 106'.

Referring again to FIGS. 3A and 3B, movable press 120 is used to deform the shield member 106 prior to trimming away the excess portion 117 to produce an interfacing seam area along inner surface 108 within the outer profile defined by sidewall outer surface 110. As will become apparent, a seam area extending interiorly to an outer tangent point of the original bend outer surface 115 is produced by deforming inner surface 108. Creation of the interiorly existing seam area results in less protrusion of the exterior surface of the housing along the seam. Press 120 includes a protruding member 122 that presses down on inner surface 108 exteriorly to and adjacent to bend 150, to force the shield material to deform interiorly, reducing the arc length of bend inner surface 114 and reducing the original bend inner radius 116.

Figure 5:
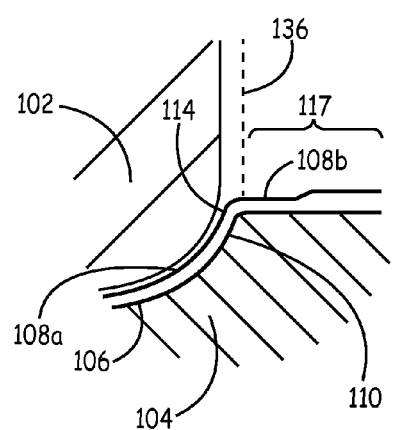
FIG. 5 is a conceptual diagram of a housing shield member after deformation along an inner surface to form a seam area.

FIG. 5 is a conceptual diagram of the shield member 106 after deformation by press 120. The inner surface 108 of shield member 106 can be referred to as having two portions: an interior portion 108a that extends inward from and includes an interior portion of bend inner surface 114 and an exterior portion 108b that extends outward from bend inner surface 114 and includes excess portion 117 prior to trimming. The interior portion 108a will define at least a portion of the interior surface of the IMD housing. The exterior portion 108b becomes the seam area and includes the excess portion 117 that is trimmed away. Press 120 is advanced downward against the exterior portion 108b of shield member inner surface 108 to produce a seam area as further described below.

During the deformation of the exterior portion 108b, shield member 106 is stabilized along its outer surface 110 by fixed support die 104 and stabilized along the interior portion 108a of inner surface 108 by fixed clamping die 102.

The inner surface exterior portion 108b is depressed and deformed such that shield material is deformed interiorly, reducing the original inner radius 116 and the arc length of bend inner surface 114. After withdrawing press 120, excess portion 117 is trimmed away by a vertical cut through shield member 106 indicated by dashed line 136. A vertical cut can be made while shield member 106 remains held within dies 102, 104 without moving shield member 106 to a different fabrication station. The vertical trimming can be made tangential or nearly tangential to the minor sidewall 113 along outer surface 110 such that a minor or no projection from the minor sidewall 113 remains. Any minor projections along the trimmed edge may be incorporated in a weld pool when shield member 106 is coupled to a second shield member 106', resulting in a substantially smooth exterior surface of the IMD housing.

As used herein, a "nearly tangential" cut refers to a cut made less than approximately one shield thickness 112 exteriorly from the outer profile of outer surface 110. A "minor projection" and "substantially smooth" exterior surface refer to an exterior surface having an exterior projection along the seam that extends less than the shield thickness. For example, the exterior edge of the seam may extend less than approximately 75% of the shield thickness. In other examples, an exterior projection along the seam extends less than approximately 25% the shield thickness 112. In still other embodiments, an exterior projection along the seam extends less than approximately 10% of the shield thickness. As used herein, the term "approximately" is defined as ±10% of the stated value unless otherwise stated. A minor projection may be present along the exterior of the seam due to the specification tolerance of the trim location 136 relative to outer surfaces 110 and 110'. In other embodiments, a minor projection may be required to meet a specified minimum width of seam area 142.

Figure 6A:
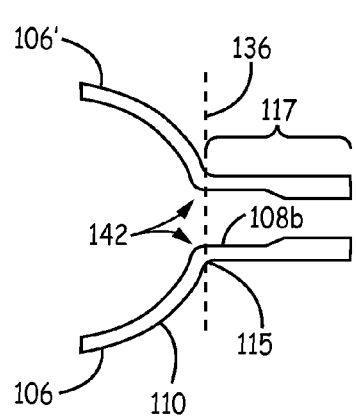
FIG. 6A is a conceptual view of shield members after deformation.

FIG. 6A is a conceptual view of shield members 106, 106' after deformation by movable press 120 indicating the trim location 136 tangential or nearly tangential to the outer profiles of respective outer surfaces 110, 110'. Trim location 136 may be along an exterior portion of bend outer surface 115 or immediately adjacent thereto such that no excess material protrudes exteriorly from outer surface 110 after trimming. Deformation of exterior portion 108b of inner surface 108 produces a directly mating seam area 142 between shield members 106 and 106'. Seam area 142 extends along inner surface 108, within the outer profile of the outer surface 110, and interiorly to bend outer surface 115.

Figure 6B:
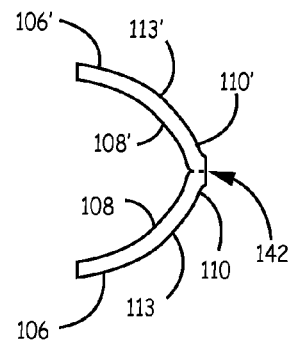
FIG. 6B is a conceptual view of shield members after trimming excess material.

FIG. 6B is a conceptual view of shield members 106 and 106' after trimming the excess portion 117 at trim location 136 and positioning inner surfaces 108, 108' together along the seam area 142. The direct contact of the inner surfaces 108 and 108' along the seam area 142 that is made possible by deformation of the exterior portion 108b of inner surface 108 produces a sufficient interface for reliably sealing the shield members 106 and 106' together within the outer profile of sidewalls 113, 113' defined by outer surfaces 110, 110'.

Figure 6C:
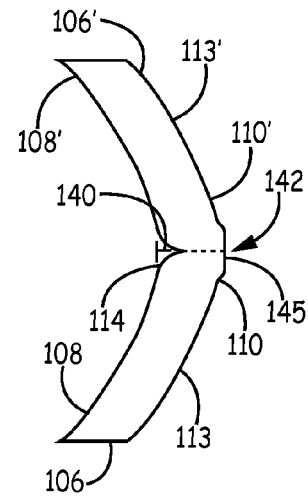
FIG. 6C is an enlarged view of the interface along a seam area between the trimmed shield members of FIG. 6B.

FIG. 6C is an enlarged view of the interface at seam area 142 between the trimmed shield members 106, 106'. The open gap that would normally be present along inner surface bend 114 has been significantly reduced, to nearly negligible in some examples, by deforming shield material interiorly to produce seam area 142 along inner surface 108 and wholly within the outer profile of the outer surface 110 of sidewall 113 after trimming tangentially to outer surface 110. In other embodiments, at least a majority of the seam exists within the outer profile of outer surface 110, with an exteriorly protruding seam portion that is less than one thickness 112 of the shield material. The original inner radius 116 of bend 150 has been reduced from at least 1.5 times the shield thickness 112 prior to deformation to less than 1.5 times the shield thickness 112, and in some examples less than the shield thickness. The distance 140 from the interior edge of inner surface bend 114 to the point at which inner surfaces 108 and 108' come into direct contact (at an inner edge of seam area 142) is significantly shorter than the distance 132 prior to deformation of the exterior portion 108b of inner surface 108 as shown in FIG. 4. The seam area 142 may be laser welded to join the shield members 106 and 106' along the directly contacting seam area 142 between inner surfaces 108, 108'.

The resulting seam is characterized by a continuously smooth or minor projection 145 along exterior surface of the seam area 142 and a bend inner surface 114 extending interiorly from the inner seam edge having a relatively small radius, e.g. a radius less than the shield thickness 112. The minor projection 145 protrudes less than 75% of the shield thickness 112. In other examples, the minor projection 145 extends no more than approximately 25% of the shield thickness and may be less than 10% of the shield thickness.

Figure 7:
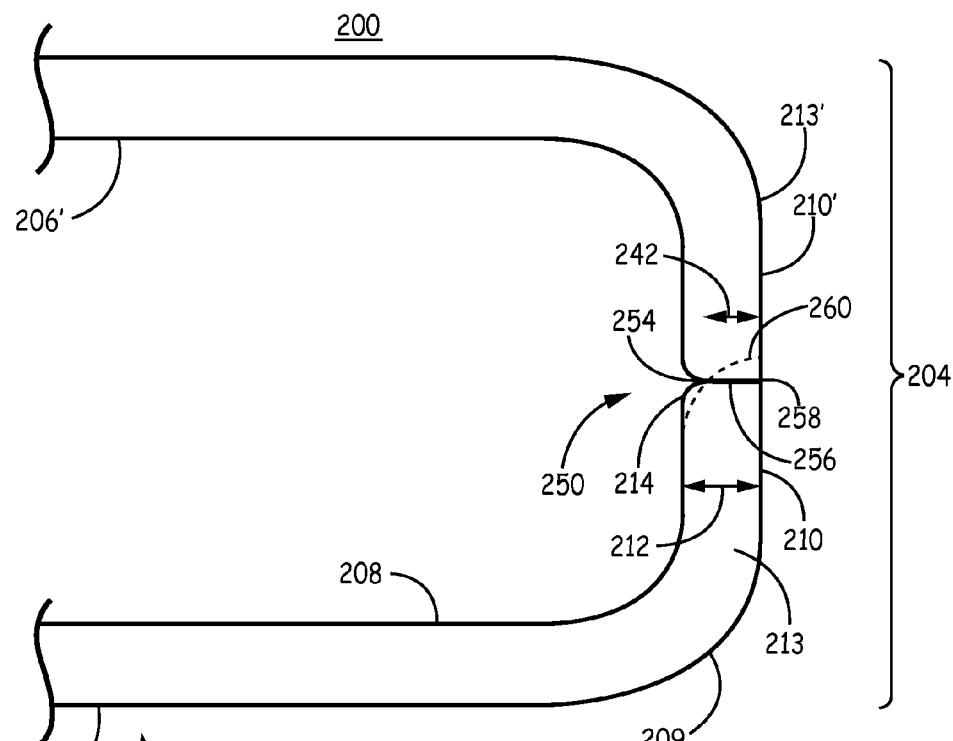
FIG. 7 is an enlarged, partial sectional view of an IMD housing according to another example.

FIG. 7 is an enlarged, partial sectional view of an IMD housing 200 according to another example and depicting aspects of a seam between two shield portions formed using the methods disclosed herein. Housing 200 includes a first shield member 206 and a second shield member 206'. First shield member 206 has an inner surface 208 and an outer surface 210 separated by a shield thickness 212. First shield member 206 has a side 202, which may be a major side of IMD housing 200. A bend 209, which may be formed by stamping the shield material as described above, extends from side 202 to a sidewall 213. Sidewall 213 may be a minor sidewall of shield member 206 and define a portion of a minor sidewall 204 of housing 200 in some examples. An outward bend 250 of sidewall 213 is defined by a bend inner surface 214. The inner surface 208 of shield member 206 is deformed exteriorly to bend 250, as described above, to displace shield material interiorly and reduce the arc length and radius at bend inner surface 214, thereby producing seam area 242. At least a majority of seam area 242 resides interiorly to the outer profile of sidewall 213 defined by outer surface 210.

For comparison, dashed line 260 approximates the profile of the original outward bend 250 prior to deformation. The relatively longer arc length and greater radius of the original bend inner surface 214 prior to deformation would require a seam area beginning near or exteriorly to the outer surface 210 of sidewall 213, such that a majority of the seam area would reside exteriorly to the outer profile of sidewall 213.

After deforming inner surface 208 along the original inner surface bend 214 to produce seam area 242, a seam 256 is formed along seam area 242 to seal shield member 206 to shield member 206', for example by welding. Shield member 206' is a mirror image of shield member 206 in this example. Shield member 206' includes a sidewall 213' having an outer profile defined by shield member outer surface 210'. Housing minor sidewall 204 includes shield member sidewalls 213 and 213' and seam 256. Seam 256 extends from an interior edge 254 to an exterior edge 258. Exterior edge 258 is flush with the outer surfaces 210, 210' of respective shield members 206, 206' such that seam 256 is a non-protruding seam. In other words, seam area 242, and consequently seam 256, does not extend exteriorly from the outer profile of sidewalls 213 and 213' defined by flush outer surfaces 210, 210'. The seam area 242, and consequently seam 256, resides wholly within the outer profile defined by sidewalls 213, 213' such that a substantially smooth continuous housing sidewall 204 is formed by shield members 206 and 206' without any protruding edges in the vicinity of seam 256.

In other examples, a majority of seam area 242, and consequently a majority of seam 256 resides within the outer profile of sidewalls 213 and 213' with a minority of seam 256 extending exteriorly to outer surfaces 210 and 210'. As described above, a minor projection may remain along the exterior seam edge 258 that extends outward from outer surfaces 210, 210' less than approximately 75% of the shield thickness 212.

In housing 200 and other housing examples described herein, the seam 256 joining two shield members 206 and 206' is between the inner surfaces 208 and 208' of the shield members as opposed to being between end faces of the shield members, e.g. end faces formed by cutting through sidewall 213 and 213'. The seam is along the deformed inner surface bend 214. As such, the resulting housing 200 is characterized by an inner surface bend 214 extending interiorly from the interior edge 254 of the seam 256, where the deformed inner surface bend has a bend radius less than one shield thickness 212.

Figure 8A:
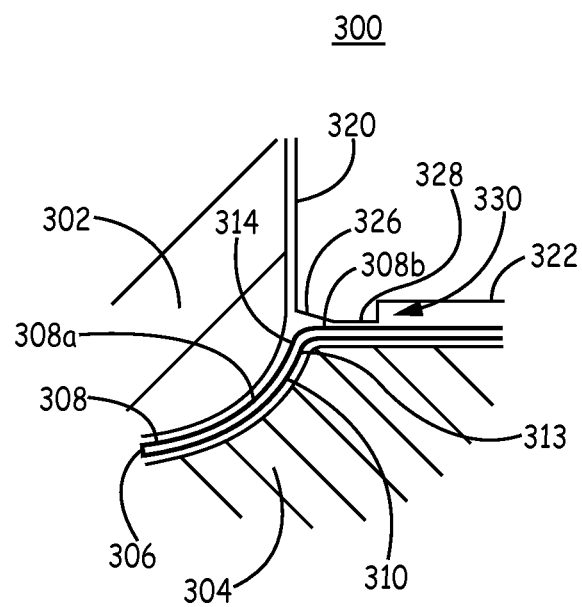
FIG. 8A is a conceptual diagram of an alternative embodiment of movable press for deforming a shield member for producing a seam area along a shield member inner surface.

FIG. 8A is a conceptual diagram 300 of an alternative embodiment of the movable press 320 used to deform a shield member 306 for producing a seam area along the exterior portion 308b of inner surface 308. A fixed support die 304 supports shield member outer surface 310, and a fixed clamping die 302 supports shield member inner surface 308 along interior portion 308a of inner surface 302. Movable press 320 is advanced against exterior portion 308b of inner surface 308.

Press 320 may have numerous geometries to cause inward deformation of exterior portion 308b to produce a desired seam area. The seam area is generally produced by shifting shield member material interiorly toward inner surface bend 314 to produce a majority of the seam area residing within the outer profile of the sidewall 313. The seam area, however, is not necessarily flat as generally portrayed in FIG. 6A. The seam area may be angled or have features such as a ridge, groove, bump, indent, or other recessed or protruding feature that mates with a corresponding feature of the second shield. Such features may facilitate alignment of the shield members and/or facilitate the sealing process. For example, an angled seam area or a seam area having an interior ridge or bump may serve to at least partially block or otherwise reduce laser welding energy directed interiorly that might otherwise damage IMD internal components. If adhesive or another sealing material is used along the seam area, a groove, ridge or other feature may prevent excess material from entering the interior cavity of the IMD housing.

Figure 8B:
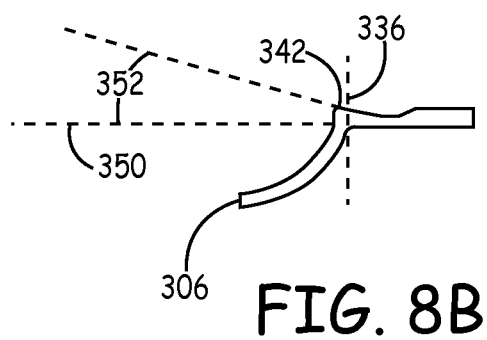
FIG. 8B is a partial side sectional view of the shield member of FIG. 8A after deformation of the inner surface.

In the example shown, press 320 includes a "foot" 330 extending downward from a lower surface 322. Foot 330 includes an angled portion 326 and a flat portion 328. Angled portion 326 provides space over bend inner surface 314 to encourage shield material to be preferentially deformed interiorly rather than exteriorly. When press 320 is advanced downward against exterior portion 308b of inner surface 308, the inner surface 308 is deformed to produce an angled seam area 34, as shown in FIG. 8B. Seam area 342 is angled with respect to a central axis 350 of the shield member 306. For example, exterior portion 308b of inner surface 308 may be deformed at an angle 352 of up to forty-five degrees relative to central axis 350.

Shield member 306 may be trimmed along outer surface 310 tangential to or nearly tangential to minor side 313 as indicated by dashed line 336. The angled seam area 342 can serve as a barricade or block that decreases laser welding energy entering the internal housing cavity, which could otherwise potentially damage internal IMD components during welding of the seam area 342. While not explicitly shown, it is recognized that a second shield member for mating with member 306 would be deformed with an inverse mating angle for directly interfacing with member 306 along angled seam area 342. In other embodiments, the seam area 342 may be deformed to include interlocking surface geometries, such as a bump, ridge, dimple, groove or other protruding or recessed features that mate with an adjoining seam area of a second shield member.

Figure 9A:
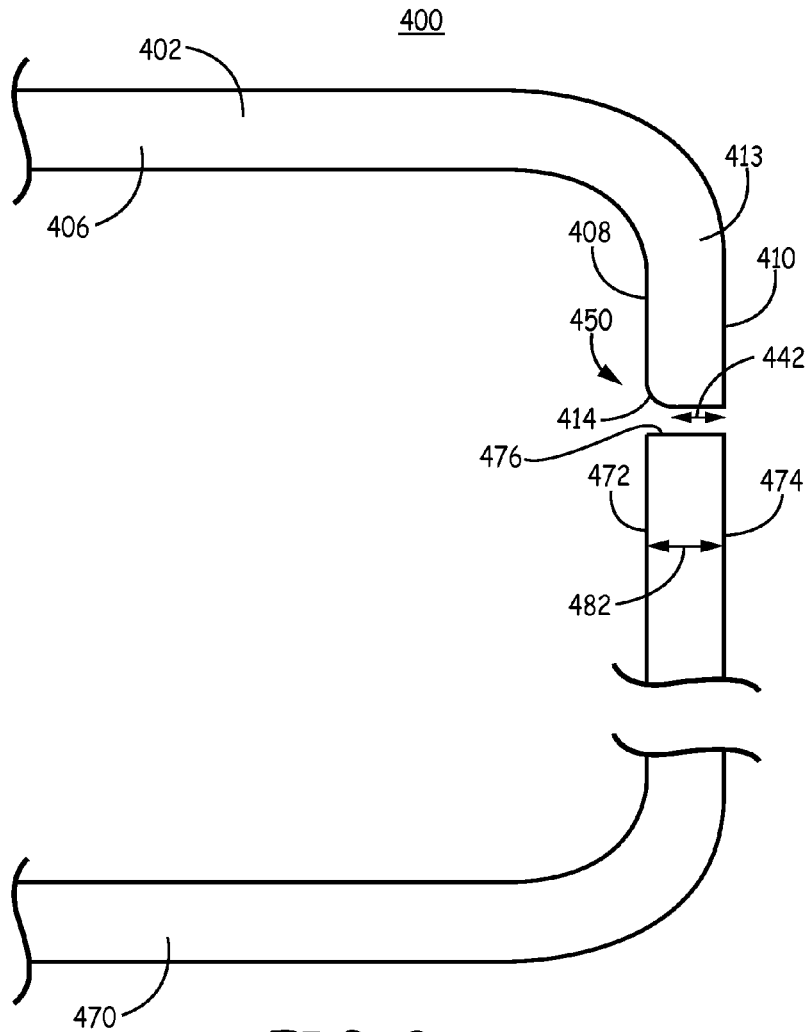
FIG. 9A is an enlarged, partial side sectional view of an alternative embodiment of an IMD housing.

FIG. 9A is an enlarged, partial sectional view of an alternative embodiment of an IMD housing 400. A first shield member 406 generally corresponds to shield member 206, described above, having a first side 402, a sidewall 413 extending from the first side 402, and an outward bend 450 extending from the sidewall 413 defined by a bend inner surface 414. A seam area 442 extends along the inner surface 408 of shield member 406, exterior to bend inner surface 414 and interiorly to outer surface 410. As described above, deformation of the inner surface 408 along the original outward bend 450 produces a seam area 442 residing within the outer profile of sidewall 413 defined by shield member outer surface 410.

A second shield member 470 has an inner surface 472 and an outer surface 474 separated by a shield thickness 482. Shield member 470 has an end face 476 extending from inner surface 472 to outer surface 474. Shield member 470 may be a stamped or molded member having end face 476 produced by trimming or cutting through the shield material from the outer surface 474 to the inner surface 472, for example. End face 476 is therefore not an extension of the inner surface 472 in the way that seam area 442 is a continuation of inner surface 408 along deformed outward bend 450.

Figure 9B:
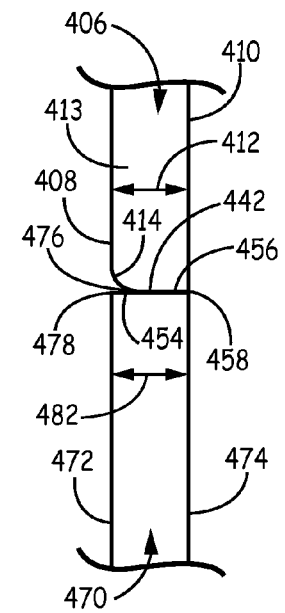
FIG. 9B is a partial sectional view of the housing shown in FIG. 9A after coupling shield members along a seam.

FIG. 9B is a partial sectional view of the housing 400 shown in FIG. 9A. In FIG. 9A, the shield members 406 and 470 are shown prior to joining at seam area 442 and end face 476. The shield member 406 and 470 are shown coupled together in FIG. 9B along seam 456. Seam 456 is formed between seal area 442 and end face 476, e.g. by welding. Seam 456 resides wholly within an outer profile of shield member 406 defined by outer surface 410 of sidewall 413. In other examples, a majority of seam 458 resides within the outer profile of sidewall outer surface 410. As described above, a minor projection may exist along the exterior seam edge 458.

As shown by FIGS. 9A and 9B, the first shield member 406 may be formed using the methods described above to deform an inner surface 408 to produce a seam area 442 while the second shield member 470 may be formed using other techniques. Seam 458 is between the inner surface seam area 442 on the first shield member 406 and the end face 476 of the second shield member 470. Alternatively the seam is between the inner surface seam area 442 of the first shield member 406 and an inner surface of the second shield member, for example when the second shield member is a substantially flat lid placed against shield member 406 along seam area 442.

Outer surface 474 of shield member 470, outer surface 410 of shield member 406, and outer edge 458 of seam 456 define a substantially smooth exterior surface of housing 400, with no projection along seam outer edge 458, or in some cases a minor projection along seam outer edge 458 as described above. Shield member 470 may have an interior corner 478, at the intersection of inner surface 472 and end face 476, after sealing shield member 470 and 406. Shield member 406 has a bend inner surface 414 along the deformed outward bend 450 that is reduced in arc length and radius compared to the original outward bend of shield member 406 prior to deforming inner surface 408 in the manner described above. Bend inner surface 414 extends interiorly from inner seam edge 454 such that the resulting width of seam area 442 from inner seam edge 454 to outer seam edge 458 may be slightly less than the shield thickness 412. In other examples, a minor projection (not shown in FIG. 9B) may extend exteriorly less than 50% of the shield thickness 482 so that the seam width from inner edge 454 to outer edge 458 is at least equal to the shield thickness 482.

Figure 10:
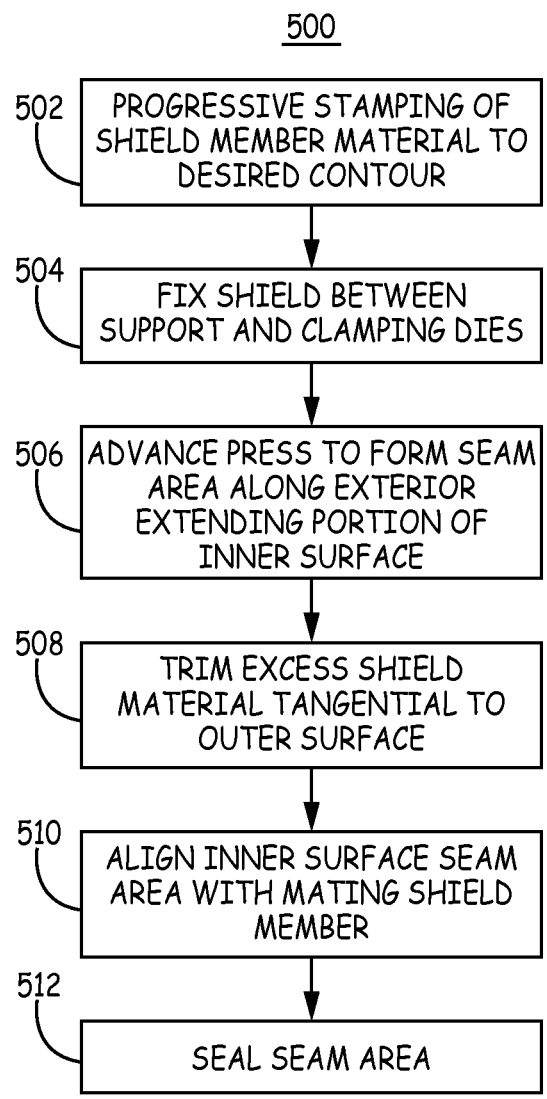
FIG. 10 is a flow chart of an example method for manufacturing an IMD housing.

FIG. 10 is a flow chart 500 of a method for manufacturing an IMD housing according to techniques disclosed herein. At block 502, a selected housing/shield material, such as any of the examples listed above, is stamped or machined into a desired contour to form a shield member. In one embodiment, the shield member is formed in a progressive stamping process using multiple dies as described previously. The shield member is fixed between a support die and a clamping die at block 504. At block 506, a movable press is advanced against the shield material inner surface. The press is advanced to deform an exterior portion of the inner surface, along an outward bend of the shield member, to produce a seam area. This deformation may be performed in one step or in multiple steps by advancing the movable press in steps and/or shifting the movable press along the shield inner surface. As described above, the deformation may include producing an angled seam area or a raised or recessed feature along the seam area.

After forming the seam area, excess shield material is trimmed away by cutting through the shield material tangential (or nearly tangential) to the outer surface that defines an outer profile of a shield side. In one example, a progressive stamping operation is performed at block 502 to produce the desired contour in the shield member using a set of support dies. Upon reaching the final desired contour, the last support die and a clamping die are fixed in position to support the shield member, and the seam area is formed at block 506 by advancing a press along an exterior portion of the shield member inner surface. The press is raised, and a cutting blade or laser is used to trim excess shield material while the shield member remains held in place by the support and clamping dies at block 508.

All steps of forming the shield contoured shape, deforming the inner surface to produce a seam area, and trimming excess material are performed at a single fabrication station in one example. Transfer of the shield member to a different station for trimming is not required since the exterior portion of the inner surface is accessible for trimming via a vertical (top down) cut in the manner described in conjunction with FIG. 5.

At block 510, the shield member is removed from the clamping and support dies and aligned with a second shield member by placing the seam area produced at block 506 in direct contact with a seam area of the second shield member. The first and second shield members are coupled together along the seam area at block 512. For example, the seam area may be sealed at block 512, e.g. using laser welding or other appropriate sealing method depending on the shield material being used and sensitivity of internal components assembled in the IMD housing. It is understood that prior to coupling the first and second shield members together, internal device components may be assembled within one or both shield members.

Thus, an IMD housing and associated apparatus and method for manufacture have been presented in the foregoing description with reference to specific embodiments. It is appreciated that various modifications to the referenced embodiments may be made without departing from the scope of the disclosure as set forth in the following claims.

The invention claimed is:

1. A medical device housing having an exterior surface and an interior surface, the interior surface defining a cavity for enclosing medical device components, the housing comprising:
   a first shield member having an inner surface and an outer surface spaced apart by a shield thickness, the inner surface comprising a depressed portion;
   a second shield member having an inner surface and an outer surface; and
   a seam coupling the first shield member inner surface to the second shield member along a seam area comprising the depressed portion of the first shield member inner surface, the seam having an interior edge and an exterior edge,
   the first shield member inner surface comprising a bend extending exteriorly to the seam interior edge, the bend comprising interiorly deformed first shield member material from the depressed portion of the inner surface of the first shield member.

2. The housing of claim 1, wherein the seam exterior edge projects less than the shield thickness from the first shield member outer surface and the second shield member outer surface.

3. The housing of claim 1, wherein the bend has a radius less than 1.5 times the shield thickness.

4. The housing of claim 1, wherein the first shield member comprises:
   a sidewall having an outer profile defined by the first shield member outer surface; and
   a majority of the seam area residing interiorly to the outer profile of the sidewall.

5. The housing of claim 1, wherein the second shield member comprises an end face extending from the inner surface to the outer surface,
   the seam coupling the first shield member inner surface to the second shield end face.

6. The housing of claim 1, wherein the seam couples the first shield inner surface to the second shield inner surface.

7. The housing of claim 1, wherein the housing comprises a major side and a minor side and the seam extends at least along a major side of the housing.

8. The housing of claim 1, wherein the housing comprises opposing major sides separated by a minor sidewall and the seam extends only along the minor sidewall.

9. The housing of claim 1, wherein the seam area comprises one of an angled portion, a recessed portion and a raised portion.

10. The housing of claim 1, wherein the first shield member comprises a sidewall having an outer profile defined by the first shield member outer surface;
    wherein the seam exterior edge projects less than one half of the shield thickness from the outer profile,
    a majority of the seam area residing interiorly to the outer profile.

11. The housing of claim 1, wherein the bend comprising the interiorly deformed first shield material having at least one of a radius and an arc length that are smaller than a respective one of a previous radius and a previous arc length of the bend prior to the shield material being interiorly deformed from the depressed area of the first shield member inner surface.

12. A medical device, comprising:
    a housing having an interior surface defining a cavity for enclosing medical device components and an exterior surface separated from the interior surface by a wall thickness,
    the housing further comprising:
    a first shield member having an inner surface and an outer surface spaced apart by a shield thickness and comprising a depressed portion of the inner surface;
    a second shield member having an inner surface and an outer surface; and
    a seam coupling the first shield member inner surface to the second shield member along a seam area, the seam having an interior edge and an exterior edge,
    the first shield inner surface having a bend extending exteriorly to the seam interior edge, the bend comprising interiorly deformed first shield member material from the depressed portion of the inner surface of the first shield member; and
    the seam area comprising the depressed portion of the first shield member inner surface.

* * * * *